ROSE PLANT
Filed Oct. 23, 1965 2 Sheets-Sheet 1
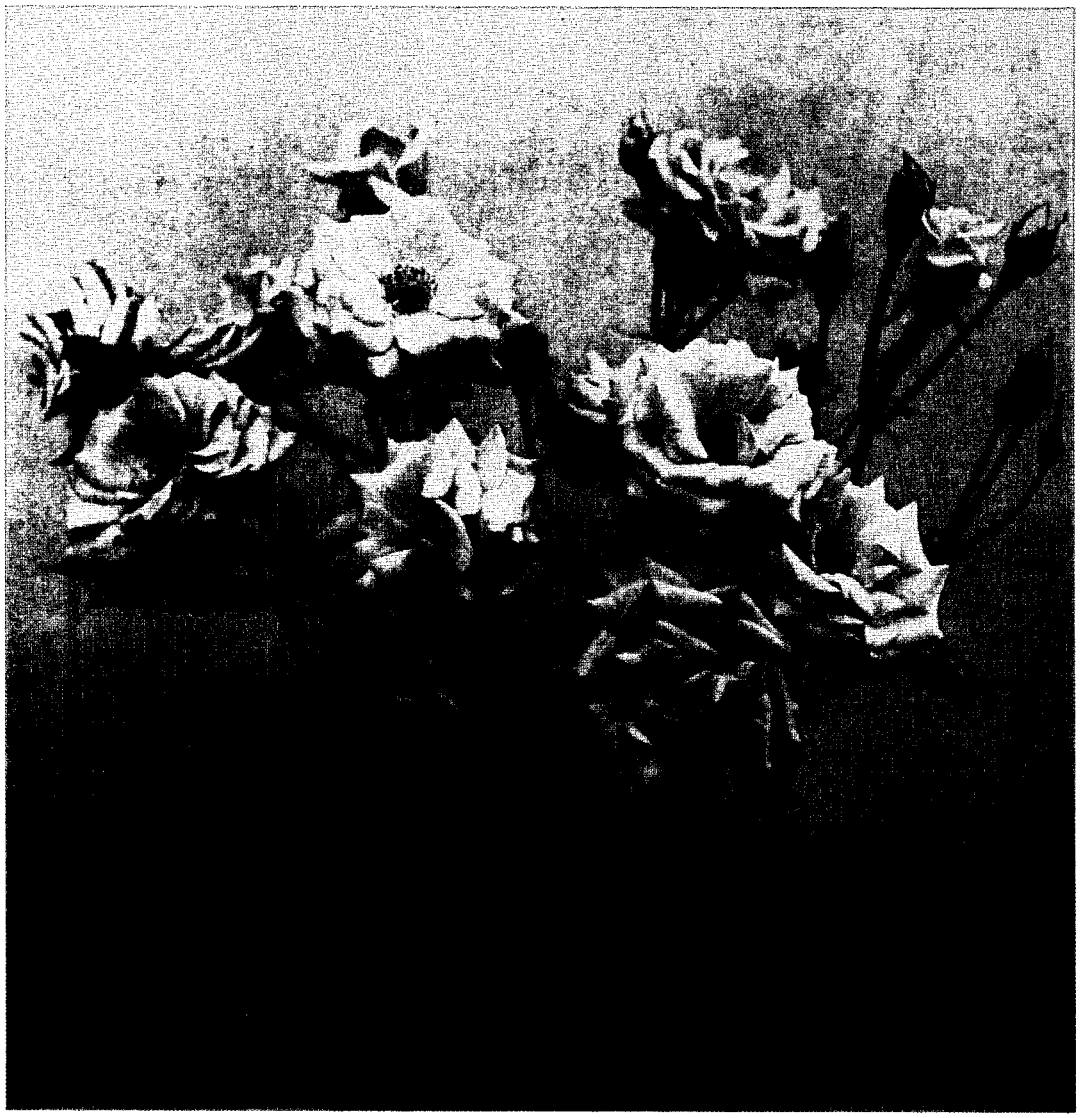

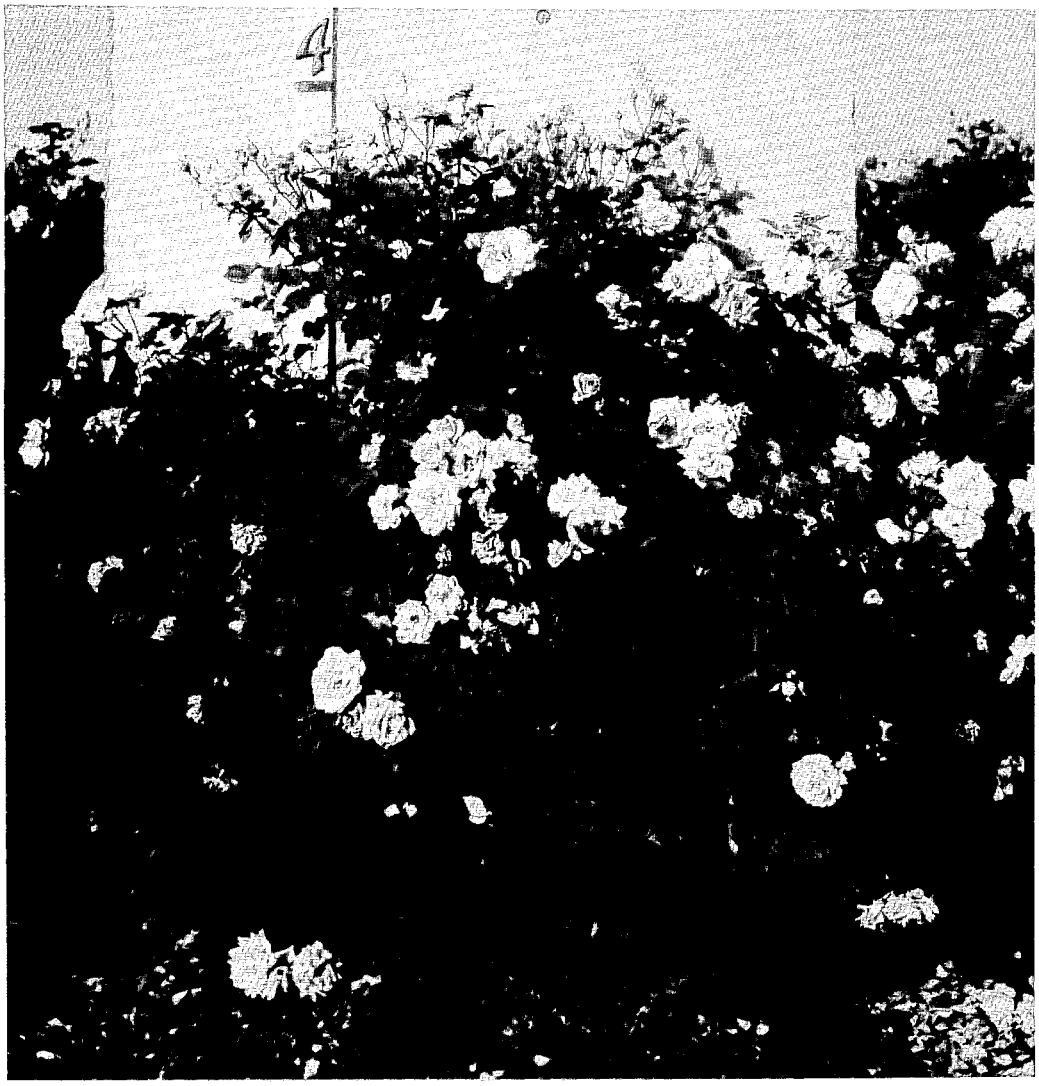
4

United States Patent Office

Plant Pat. 2,722
Patented Feb. 28, 1967

2,722
ROSE PLANT

Walter E. Lammerts, Livermore, Calif., assignor to Amling-Devor Nurseries, Inc., Livermore, Calif., a corporation of California Filed Oct. 23, 1965, Ser. No. 504,278
1 Claim. (Cl. Plt.—26)

The invention relates to a new and distinct variety of rose plant of the floribunda class, originated by me in May 1954 as a consequence of a breeding program begun in 1953. The parentage of my new rose plant is as follows: Pinocchio (Plant Patent 484), the seed parent × Queen Elizabeth (Plant Patent 1,259) the pollen parent.

The object of the cross was to combine the vigor and rate of growth of Queen Elizabeth with the floriferousness and perfection of flower form of Pinocchio and also to obtain a softer pink flower than Queen Elizabeth with a more durable and more intense pigmentation than Pinocchio by utilizing the recessive pelargonidin gene present in Queen Elizabeth in combination with the cyanidin genes of Pinocchio. The objectives were achieved along with other desirable improvements, as evidenced by the following unique combination of characteristics which are outstanding in the new variety and which distinguish it from its parents as well as from all other varieties of which I am aware. My new variety is primarily characterized by: a soft pink carmine rose color of the bloom with little or no magenta tone developing on aging; large clusters of well spaced flowers of medium size produced in greater abundance than either parent; a vigorous, dense, compact, well rounded plant habit; and an unusually rapid succession of blooming periods.

Asexual reproduction of my new variety by budding, through a series of annual propagations at Livermore and Shafter, California shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observations of field grown two year plants at Livermore, California, test garden plants at Shafter, California, and plants grown in containers in greenhouses at Santa Rosa, California during 1964.

Plant upright, full, compact, heavily branched, to 3–4 feet. The stems slender but strong; supple but erect, red when young, becoming green at maturity. The individual young stems grow in a conspicuously zig-zag manner characteristic of the variety "Garnette." Except for the few thorns, the stems are glabrous, sub-nitid and smooth. Thorns few, on some stems entirely lacking, rarely more than 3–4 per internode, scattered, long, slender, sharp-pointed, straight to somewhat recurved, about 3/8–7/16" long, red when young, straw to grey when old, strong and needlelike, the tips translucent. The base of the thorns decurrent about 3/8" long 3/32" broad. The thorn proper about 1/8" broad, about 1/32" wide. Internodes 7–11 from axil to inflorescence 1–1½" long (up to 2" under glass). Third internode below the inflorescence about 1/8" in diameter.

The leaves are large, red-bronze to burnished green (Spinach Green HCC 0960/2) above overlain chrysanthemum crimson (HCC 824/3) when young; dark green (Spinach Green HCC 0960) above, light green (HCC 0960/3) below when mature; imparapinnately compound; leaflets five except immediately below the inflorescence and occasionally the most proximal leaves of each branch. The leaf base stipulate, semi-clasping; the petiole and rachis ascending, accentuating the zig-zag internode pattern; the stipules well developed, auriculate; the margins fimbriate; the auriculae moderately ornate to fimbriate, sub-patent. The rachis is armed below, grooved above, the edges of the grooves ciliate with many small prickles; green below, red-brown above. The thorns of the rachis well developed, about 1/16"–1/8" long, usually associated with the leaflets.

The leaflets broadly ovate, coarsely serrate, large, leathery, sub-rugose, of three sizes with the terminal being largest, about 2½" long x 1¾" wide, the center pair about 1¾" long x 1⅝" wide and the proximal pair about 1⅜" x 1". The margin somewhat doubly serrate. The primary teeth coarse about 1/16" long and 1/8" across the base or somewhat smaller. The secondary serrations fine or lacking, tips of the leaves acute to acuminate.

The inflorescence is corymboid compound, usually bearing three flowers all arising from essentially the same point. The lateral pair are borne on short stems of 2–3 nodes and slightly exceed the terminal peduncle in length.

The floriferous stems are subtended by bracts often conspicuously foliaceous, sometimes compound, usually; when highly reduced, appendaged at their tips, the appendages finely serrate to fimbriate. Bracts of the lateral flowers lanceolate, the lowermost with functional axillary buds.

The peduncles reddish, slender but stiff, erect and strong, pubescent when young, never armed, about 2–2¾" long, 1/16–3/32" in diameter. The pubescence moderate to sparse, dehiscent, extremely fine, hyaline about 1/64" long, heaviest distally. The hypanthium narrowly urceolate, green, pubescent, about ¼" long and 5/16" in diameter at the top. Sepals five, lanceolate, about 9/32" wide x ⅞" long, margins usually ornate, the appendages foliaceous. The bases of the sepals marked red. The petals numerous, 20–25, gradually becoming staminoidal centripetally; staminoids 10–12. The petals pink, Neyron rose (HCC 623/1) to Spinel Pink (HCC 0625) above and Tyrian Rose (HCC 24/2) to Spinel Pink (HCC 625/1) below, broadly obovate entire, acuminate; the largest, about 1¼" x 1¼" at anthesis with a small isoscelean ivory eye at the base about ¼" across, the color at anthesis is uniform above and below.

The mature petals are larger, about 1⅞–2" long x 1½" across, obovate, entire, acuminate, especially the inner petals, the margins are rolled downward and under giving the blossom a sculptured look. The color is light Carmine Rose (HCC 621/3) to Rose Pink (HCC 427/1) above and Neyron Rose (HCC 623/3) to Rose Pink (HCC 427) below. The stamens are about 70–75 in number. The filaments are about ¼–⅜" long reddish, curved, white distally; the anthers are Saffron Yellow (HCC 7/1), about 3/32" long x 1/16" wide. Pistils about 30–35, ⅝" long, or less. The stigmas are capitate fimbriate, white, about 3/128" in diameter. The styles are filiform, about ½" long or less, red below the stigma, white proximally, pubescent distally, the pubescence hyaline, silky. The ovary white, about 1/8" long attenuated, about 3/64" wide at the base. The young fruit is globular, smooth with the semi-persistent sepals dehiscing in six to eight weeks.

Having thus disclosed my invention, I claim:

A new and distinct variety of rose plant of the fluoribunda class substantially as herein shown and described primarily characterized by: soft pink carmine rose color of the bloom with little or no magenta tone developing on aging; large clusters of well spaced flowers of medium size produced in greater abundance than either parent; a vigorous, dense, compact, well rounded plant habit; and an unusually rapid succession of blooming periods.

No references cited.

ABRAHAM G. STONE, *Primary Examiner.*

R. E. BAGWILL, *Assistant Examiner.*